United States Patent
Bosua (10) Patent No.: US 12,007,338 B2
(45) Date of Patent: Jun. 11, 2024

(54) IN VITRO SENSOR FOR ANALYZING IN VITRO FLOWING FLUIDS

(71) Applicant: Know Labs, Inc., Seattle, WA (US)

(72) Inventor: Phillip Bosua, Seattle, WA (US)

(73) Assignee: KNOW LABS INC., Seattle, WA (US)

( * ) Notice: Subject to any disclaimer, the term of this patent is extended or adjusted under 35 U.S.C. 154(b) by 330 days.

(21) Appl. No.: 17/468,298

(22) Filed: Sep. 7, 2021

(65) Prior Publication Data

US 2022/0074870 A1 Mar. 10, 2022

Related U.S. Application Data

(60) Provisional application No. 63/076,030, filed on Sep. 9, 2020.

(51) Int. Cl.
| | | |
|---|---|---|
| *G01N 22/00* | (2006.01) | |
| *G01N 33/487* | (2006.01) | |
| *G01S 13/02* | (2006.01) | |
| *G01S 17/02* | (2020.01) | |

(52) U.S. Cl.
CPC ........... *G01N 22/00* (2013.01); *G01N 33/487* (2013.01); *G01S 13/02* (2013.01); *G01S 17/02* (2013.01)

(58) Field of Classification Search
CPC ...... G01N 22/00; G01N 33/487; G01S 13/02; G01S 17/02
See application file for complete search history.

(56) References Cited

U.S. PATENT DOCUMENTS

| | | | |
|---|---|---|---|
| 4,202,000 A | 5/1980 | Carballes | |
| 7,295,827 B2 | 11/2007 | Liu et al. | |
| 7,846,311 B2 | 12/2010 | Feldman et al. | |
| 8,223,021 B2 | 7/2012 | Goodnow et al. | |
| 8,882,670 B2 | 11/2014 | Hancock | |
| 9,041,920 B2 | 5/2015 | Mander et al. | |
| 9,198,607 B2 | 12/2015 | Fischer | |
| 9,864,024 B2 | 1/2018 | Vester | |
| 9,869,636 B2 | 1/2018 | Mander et al. | |

(Continued)

FOREIGN PATENT DOCUMENTS

| | | |
|---|---|---|
| CN | 104739419 | 7/2015 |
| CN | 204995483 U | 1/2016 |

(Continued)

OTHER PUBLICATIONS

Hanna, J. et al., "Noninvasive, wearable, and tunable electromagnetic multisensing system for continuous glucose monitoring, mimicking vasculature anatomy," Science Advances, 6, eaba5320, 2020 (11 pages).

(Continued)

*Primary Examiner* — Jason M Ip (74) *Attorney, Agent, or Firm* — MERCHANT & GOULD P.C.

(57) ABSTRACT

Apparatus, systems and methods of analyzing an in vitro flowing fluid using an in vitro sensor that operates using non-optical frequencies such as in the radio or microwave frequency bands of the electromagnetic spectrum. The in vitro sensor directs one or more signals that are in the radio or microwave frequency bands of the electromagnetic spectrum into an in vitro flowing fluid and detects one or more responses that result from transmission of the signal(s) into the in vitro flowing fluid.

20 Claims, 5 Drawing Sheets

(56) References Cited

U.S. PATENT DOCUMENTS

| | | |
|---|---|---|
| 10,149,629 B2 | 12/2018 | Szczepaniak et al. |
| 10,478,101 B1 | 11/2019 | Cespedes et al. |
| 10,548,503 B2 | 2/2020 | Bosua |
| 10,617,296 B2 | 4/2020 | Sloan et al. |
| 10,856,766 B2 | 12/2020 | Leabman |
| 10,912,500 B2 | 2/2021 | Poeze et al. |
| 10,956,950 B2 | 3/2021 | Al-Ali et al. |
| 11,031,970 B1 | 6/2021 | Bosua |
| 11,033,208 B1 | 6/2021 | Bosua |
| 11,058,317 B1 | 7/2021 | Bosua |
| 11,058,321 B2 | 7/2021 | Hein |
| 11,058,331 B1 | 7/2021 | Bosua |
| 11,063,373 B1 | 7/2021 | Bosua |
| 11,193,923 B2 | 12/2021 | Bosua |
| 11,202,582 B2 | 12/2021 | Verkruijsse et al. |
| 11,234,619 B2 | 2/2022 | Bosua |
| 11,244,753 B2 | 2/2022 | Haggerty et al. |
| 11,291,374 B2 | 4/2022 | Lee et al. |
| 11,298,037 B2 | 4/2022 | Leabman |
| 11,350,830 B2 | 6/2022 | McKenna et al. |
| 11,360,188 B2 | 6/2022 | Leabman |
| 11,367,525 B2 | 6/2022 | Addison et al. |
| 11,389,093 B2 | 7/2022 | Triman et al. |
| 11,426,104 B2 | 8/2022 | Schurman et al. |
| 2003/0036713 A1 | 2/2003 | Bouton et al. |
| 2004/0065158 A1 | 4/2004 | Schrepfer et al. |
| 2004/0127777 A1 | 7/2004 | Ruchti et al. |
| 2004/0133086 A1 | 7/2004 | Ciurczak et al. |
| 2004/0235536 A1 | 11/2004 | Kim et al. |
| 2005/0230616 A1* | 10/2005 | Cameron ............... G01N 30/88 250/282 |
| 2009/0275814 A1 | 11/2009 | Watanabe et al. |
| 2010/0041969 A1 | 2/2010 | Beise |
| 2010/0072386 A1* | 3/2010 | Harra ..................... A61B 5/05 250/395 |
| 2011/0028814 A1 | 2/2011 | Petersen et al. |
| 2012/0108932 A1 | 5/2012 | Roy |
| 2013/0096396 A1 | 4/2013 | Riedel |
| 2013/0289375 A1 | 10/2013 | Fischer |
| 2014/0213870 A1 | 7/2014 | Hsu et al. |
| 2016/0051171 A1 | 2/2016 | Pikov et al. |
| 2016/0287151 A1 | 10/2016 | Margaliot |
| 2016/0361002 A1 | 12/2016 | Palikaras et al. |
| 2017/0095667 A1 | 4/2017 | Yakovlev et al. |
| 2017/0181658 A1 | 6/2017 | Dettmann et al. |
| 2017/0248530 A1* | 8/2017 | Parker ................... G01N 22/04 |
| 2018/0028824 A1 | 2/2018 | Pivonka et al. |
| 2018/0132766 A1 | 5/2018 | Lee et al. |
| 2018/0153520 A1 | 6/2018 | Esenaliev |
| 2019/0008422 A1 | 1/2019 | Leath et al. |
| 2019/0053741 A1 | 2/2019 | Chaudhry |
| 2019/0104939 A1 | 4/2019 | Costantine et al. |
| 2019/0269853 A1 | 9/2019 | Doyle et al. |
| 2019/0290161 A1 | 9/2019 | Chase |
| 2019/0353752 A1 | 11/2019 | Lin et al. |
| 2019/0357800 A1 | 11/2019 | Bosua |
| 2019/0374135 A1 | 12/2019 | Poeze et al. |
| 2019/0388000 A1 | 12/2019 | Costantine et al. |
| 2020/0015708 A1 | 1/2020 | Uplinger, II et al. |
| 2020/0054255 A1 | 2/2020 | Conrad et al. |
| 2020/0057163 A1 | 2/2020 | Bromberg |
| 2020/0146584 A1 | 5/2020 | Bosua |
| 2020/0187791 A1 | 6/2020 | Leabman |
| 2020/0187792 A1 | 6/2020 | Leabman |
| 2020/0187793 A1 | 6/2020 | Leabman |
| 2020/0187812 A1 | 6/2020 | Leabman |
| 2020/0187813 A1 | 6/2020 | Leabman |
| 2020/0187814 A1 | 6/2020 | Leabman |
| 2020/0187815 A1 | 6/2020 | Leabman |
| 2020/0187816 A1 | 6/2020 | Leabman |
| 2020/0187817 A1 | 6/2020 | Leabman |
| 2020/0187818 A1 | 6/2020 | Leabman |
| 2020/0187819 A1 | 6/2020 | Leabman |
| 2020/0187820 A1 | 6/2020 | Leabman |
| 2020/0187836 A1 | 6/2020 | Leabman |
| 2020/0187837 A1 | 6/2020 | Leabman |
| 2020/0187867 A1 | 6/2020 | Leabman |
| 2020/0191909 A1 | 6/2020 | Leabman |
| 2020/0191932 A1 | 6/2020 | Leabman |
| 2020/0191933 A1 | 6/2020 | Leabman |
| 2020/0191944 A1 | 6/2020 | Leabman |
| 2020/0191945 A1 | 6/2020 | Leabman |
| 2020/0191947 A1 | 6/2020 | Leabman |
| 2020/0192426 A1 | 6/2020 | Leabman |
| 2020/0192427 A1 | 6/2020 | Leabman |
| 2020/0192428 A1 | 6/2020 | Leabman |
| 2020/0193326 A1 | 6/2020 | Leabman |
| 2020/0195197 A1 | 6/2020 | Leabman |
| 2020/0195293 A1 | 6/2020 | Leabman |
| 2020/0375549 A1 | 12/2020 | Wexler et al. |
| 2021/0186357 A1 | 6/2021 | Bosua et al. |
| 2021/0186388 A1 | 6/2021 | Bosua |
| 2021/0244308 A1 | 8/2021 | Bosua |
| 2021/0259571 A1 | 8/2021 | Bosua |
| 2021/0259592 A1 | 8/2021 | Bosua |
| 2021/0259593 A1 | 8/2021 | Bosua |
| 2022/0015695 A1 | 1/2022 | Margarito et al. |
| 2022/0031254 A1 | 2/2022 | Al-Ali et al. |
| 2022/0071523 A1 | 3/2022 | Bosua |
| 2022/0071524 A1 | 3/2022 | Bosua |
| 2022/0074871 A1 | 3/2022 | Bosua |
| 2022/0077602 A1 | 3/2022 | Bosua et al. |
| 2022/0077918 A1 | 3/2022 | Bosua et al. |
| 2022/0192494 A1 | 6/2022 | Leabman |
| 2022/0192531 A1 | 6/2022 | Leabman |
| 2022/0248984 A1 | 8/2022 | Poeze et al. |

FOREIGN PATENT DOCUMENTS

| | | |
|---|---|---|
| EP | 3146898 B1 | 11/2018 |
| EP | 3981329 A1 | 4/2022 |
| JP | 2012125382 | 7/2012 |
| JP | 2014147637 | 8/2014 |
| KR | 1020030030839 | 4/2003 |
| KR | 1020090011678 | 2/2009 |
| KR | 1020150050562 | 5/2015 |
| KR | 1020160081740 | 7/2016 |
| WO | 2017163245 | 9/2017 |
| WO | 2019071138 | 4/2019 |
| WO | 2019182638 | 9/2019 |
| WO | 2019198567 | 10/2019 |
| WO | 2019217461 | 11/2019 |
| WO | 2020006077 | 1/2020 |
| WO | 2020037171 | 2/2020 |
| WO | 2021198045 A1 | 10/2021 |
| WO | 2022026623 A1 | 2/2022 |

OTHER PUBLICATIONS

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).

International Search Report and Written Opinion for PCT/US2019/031176, mailed Aug. 23, 2019, 9 pages.

Qiang et al., "Quantitative detection of glucose level based on radiofrequency patch biosensor combined with volume-fixed structures," Biosensors and Bioelectronics 98:357-363, 2017.

Shaker, G. et al., "Non-Invasive Monitoring of Glucose Level Changes Utilizing a mm-Wave Radar System," IJMHCI, vol. 10, Issue 3 (2018): pp. 10-29.

Lien, J. et al., "Soli: Ubiquitous Gesture Sensing with Millimeter Wave Radar," ACM Trans. Graph., vol. 35, No. 4, Article 142, 19 pages (Jul. 2016).

International Search Report and Written Opinion issued for International Patent Application No. PCT/IB2020/062222, Date of mailing: Mar. 25, 2021, 7 pages.

International Search Report and Written Opinion issued for International Patent Application No. PCT/IB2021/058175, Date of mailing: Jan. 13, 2022, 11 pages.

(56) References Cited

OTHER PUBLICATIONS

Stojanovic, R. et al., "An optical sensing approach based on light emitting diodes," Journal of Physics: Conference Series 76 (2007), pp. 1-6.
Rossiter, J. et al., "A novel tactile sensor using a matrix of LEDs operating in both photoemitter and photodetector modes," Proc of 4th IEEE International Conference on Sensors (IEEE Sensors 2005), pp. 994-997.
International Search Report and Written Opinion issued for International Patent Application No. PCT/IB2021/050805, Date of mailing: May 4, 2021, 8 pages.
International Search Report and Written Opinion issued for International Patent Application No. PCT/IB2021/050838, Date of mailing: May 6, 2021, 7 pages.
International Search Report and Written Opinion issued for International Patent Application No. PCT/IB2021/057989, Date of mailing: Dec. 6, 2021, 8 pages.
G. Yaakoubi, C. Dehos, B. Martineau and J. Gonzalez, "Broadband Blood Glucose Monitoring Using Waveguides From RF to Millimeter Wave Frequencies," 2020 IEEE MTT-S International Microwave Biomedical Conference (IMBioC), 2020, pp. 1-3, doi: 10.1109/IMBIoC47321.2020.9385051. (Year: 2020).
U.S. Appl. No. 62/951,756, titled "Non-Invasive Analyte Sensor and System With Decoupled Transmit and Receive Antennas," filed Dec. 20, 2019, 40 pages.
U.S. Appl. No. 62/971,053, titled "Non-Invasive Detection of an Analyte Using Different Combinations of Antennas That Can Transmit or Receive," filed Feb. 6, 2020, 60 pages.

* cited by examiner

IN VITRO SENSOR FOR ANALYZING IN VITRO FLOWING FLUIDS

FIELD

This technical disclosure relates to apparatus, systems and methods of analyzing an in vitro flowing fluid via spectroscopic techniques using non-optical frequencies such as in the radio or microwave frequency bands of the electromagnetic spectrum.

BACKGROUND

A sensor that uses radio or microwave frequency bands of the electromagnetic spectrum for in vivo medical diagnostics is disclosed in U.S. Pat. No. 10,548,503. Additional examples of sensors that use radio or microwave frequency bands of the electromagnetic spectrum for determining analytes in liquids are disclosed in U.S. Patent Application Publication 2019/0008422 and U.S. Patent Application Publication 2020/0187791.

SUMMARY

This disclosure relates generally to apparatus, systems and methods of analyzing an in vitro flowing fluid using an in vitro sensor that operates using non-optical frequencies such as in the radio or microwave frequency bands of the electromagnetic spectrum. The in vitro sensor directs one or more signals that are in the radio or microwave frequency bands of the electromagnetic spectrum into an in vitro flowing fluid and detects one or more responses that result from transmission of the signal(s) into the in vitro flowing fluid. The term "in vitro" is intended to encompass a sensor and the fluid being outside the body of a human or animal during analysis regardless of whether the fluid being analyzed is a bodily fluid or a non-bodily fluid.

The analysis of the in vitro flowing fluid can include, but is not limited to, one or more of the following: determining the presence and/or amount of an analyte in the in vitro flowing fluid; determining a steady state condition of the in vitro flowing fluid as reflected in a steady state condition of the detected response(s); determining a change in condition of the in vitro flowing fluid as reflected in a change of the detected response(s). Other analyses are possible. A flowing fluid is a fluid that is in motion due to unbalanced forces acting on the fluid. The unbalanced forces may be due to gravity or mechanical means such as a pump or a fan, or any others means for causing motion in a fluid.

The word "fluid" as used in this description and in the claims encompasses liquids, vapor, and gases and mixtures thereof. The fluid can be a bodily fluid obtained from a human or animal body. Examples of bodily fluids can include, but are not limited to, blood, urine, saliva, and semen. The fluid can be a non-bodily fluid that is not obtained from a human or animal body. A non-bodily fluid can be a fluid used in an industrial and/or manufacturing process, or a fluid used in food processing, or other types of non-bodily fluids used in other types of industries. Examples of non-bodily fluids are too exhaustive to list in detail but can include, but are not limited to, fuel, lubricating oil, mineral oil, edible oils, hydraulic fluid, water, alcoholic and non-alcoholic beverages, food additives, acidic fluids, base fluids, paper pulp, industrial gases such as oxygen, nitrogen, and the like, and many others. In general, the fluid can be human or non-human derived, animal or non-animal derived, biological or non-biological in nature, or any other fluid that one may wish to analyze using the in vitro sensors described herein.

In one embodiment described herein, an in vitro sensing system can include an in vitro sensor that is positioned adjacent to an in vitro fluid passageway that contains an in vitro flowing fluid. The in vitro sensor can include at least one transmit antenna and at least one receive antenna, with the at least one transmit antenna positioned and arranged to transmit a signal into the in vitro flowing fluid in the in vitro fluid passageway, wherein the signal is in a radio or microwave frequency range of the electromagnetic spectrum. The at least one receive antenna is positioned and arranged to detect a response resulting from transmission of the signal by the at least one transmit antenna into the in vitro flowing fluid.

In another embodiment described herein, an in vitro sensing system can be configured to sense an analyte in an in vitro flowing fluid. The in vitro sensing system can include an in vitro sensor that is positioned adjacent to an in vitro fluid passageway that contains the in vitro flowing fluid with the analyte. The in vitro sensor can include at least one transmit element and at least one receive element, where the at least one transmit element is positioned and arranged to transmit a signal into the in vitro flowing fluid in the in vitro fluid passageway, and wherein the signal is in a radio or microwave frequency range of the electromagnetic spectrum that is between about 10 kHz to about 100 GHz. In addition, the at least one receive element is positioned and arranged to detect a response resulting from transmission of the signal by the at least one transmit element into the in vitro flowing fluid.

In another embodiment described herein, an in vitro sensing method can include positioning an in vitro sensor adjacent to an in vitro fluid passageway that contains an in vitro flowing fluid, wherein the in vitro sensor includes at least one transmit antenna and at least one receive antenna. A signal that is in a radio or microwave frequency range of the electromagnetic spectrum is transmitted from the at least one transmit antenna into the in vitro flowing fluid in the in vitro fluid passageway. In addition, a response resulting from transmission of the signal by the at least one transmit antenna into the in vitro flowing fluid is detected using the at least one receive antenna.

In another embodiment described herein, an in vitro sensing method for sensing an analyte in an in vitro flowing fluid is provided. The method can include positioning an in vitro sensor adjacent to an in vitro fluid passageway that contains the in vitro flowing fluid with the analyte, wherein the in vitro sensor includes at least one transmit element and at least one receive element. A signal that is in a radio or microwave frequency range of the electromagnetic spectrum that is between about 10 kHz to about 100 GHz is transmitted from the at least one transmit element into the in vitro flowing fluid in the in vitro fluid passageway. In addition, a response that results from transmission of the signal by the at least one transmit element into the in vitro flowing fluid is detected using the at least one receive element.

DETAILED DESCRIPTION

As used throughout this specification including the claims, the term "in vitro" is intended to refer to a sensor and the fluid being outside the body of a human or animal during analysis, regardless of whether the fluid being analyzed is a bodily fluid or a non-bodily fluid. The fluid being analyzed is a flowing fluid. A flowing fluid is a fluid that is in motion due to unbalanced forces acting on the fluid. The unbalanced forces may be due to gravity or mechanical means such as a pump or a fan, or any others means for causing motion in a fluid.

The word "fluid" as used in this description and in the claims refers to liquids, vapors, and gases and mixtures thereof. The fluid can be a bodily fluid obtained from a human or animal body. Examples of bodily fluids can include, but are not limited to, blood, urine, saliva, semen, feces, breast milk, vomit, body water, interstitial fluid, intracranial fluid, amniotic fluid, aqueous humor, bile, blood plasma, cerebrospinal fluid, chyle, chyme, endolymph, extracellular fluid, transcellular fluid, exudate, female ejaculate, gastric acid, hemolymph, lymph, mucus, pericardial fluid, perilymph, peritoneal fluid, phlegm, pus, rheum, synovial fluid, tears, transudate, vaginal lubrication, and vitreous body. The fluid can be a non-bodily fluid that is not obtained from a human or animal body. A non-bodily fluid can be a fluid used in an industrial and/or manufacturing process, or a fluid used in food processing, or other types of non-bodily fluids used in other types of industries. Examples of non-bodily fluids are too exhaustive to list in detail but can include, but are not limited to, fuel, lubricating oil, mineral oil, edible oils, hydraulic fluid, water, alcoholic and non-alcoholic beverages, food additives, acidic fluids, base fluids, paper pulp, industrial gases such as oxygen, nitrogen, and the like, and many other fluids. In general, the fluid can be human or non-human derived, animal or non-animal derived, biological or non-biological in nature, or any other type of fluid that one may wish to analyze using the in vitro sensors described herein.

The flowing fluid herein can have a liquid as a primary component, i.e. the flowing fluid is at least 50% or at least 75% or at least 90% or at least 95% liquid, with gas and/or solids included in the liquid. In another embodiment, the flowing fluid herein can have gas as a primary component, i.e. the flowing fluid is at least 50% or at least 75% or at least 90% or at least 95% gas, with liquid and/or solids included in the gas.

The flowing fluid herein can have a bodily fluid as a primary component, i.e. the flowing fluid is at least 50% or at least 75% or at least 90% or at least 95% bodily fluid, with other constituents included in the bodily fluid. In another embodiment, the flowing fluid can have a non-bodily fluid as a primary component, i.e. the flowing fluid is at least 50% or at least 75% or at least 90% or at least 95% non-bodily fluid, with other constituents included in the non-bodily fluid.

Figure 1A:
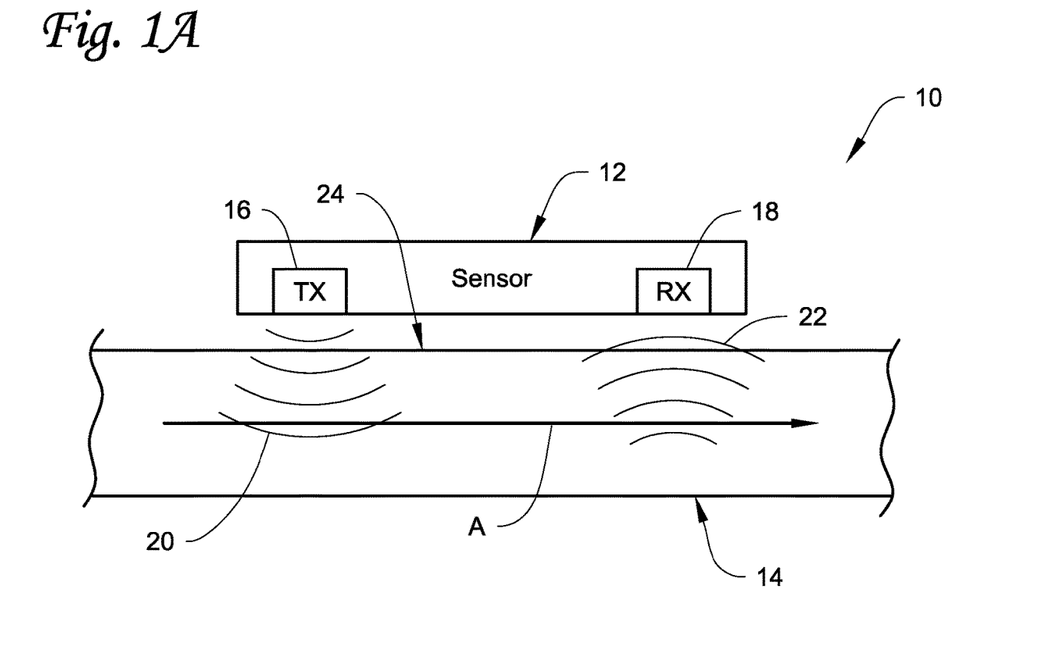
FIG. 1A is a schematic depiction of a portion of in vitro sensing system with an in vitro sensor and an in vitro fluid passageway.

With reference to FIG. 1A, an example of an in vitro sensing system 10 is illustrated. The system 10 includes at least one in vitro sensor 12 and an in vitro fluid passageway 14 through which an in vitro fluid flows as indicated by the arrow A. The in vitro sensor 12 is positioned relative to the in vitro fluid passageway 14 to permit the in vitro sensor 12 to sense the fluid flowing through the fluid passageway 14. For example, the in vitro sensor 12 can be positioned adjacent to the fluid passageway 14 and outside the fluid passageway 14. The sensor 12 can be spaced from the fluid passageway 14 so that a gap exists between the sensor 12 and the fluid passageway 14 as indicated in FIG. 1. In another embodiment, the sensor 12 may be in direct contact with the fluid passageway 14. If multiple sensors 12 are used, the sensors 12 can be spaced from one another along the fluid passageway 14 and/or the sensors 12 can be located at the same general location of the fluid passageway 14 but at circumferentially spaced locations around the fluid passageway 14.

Figure 1B:
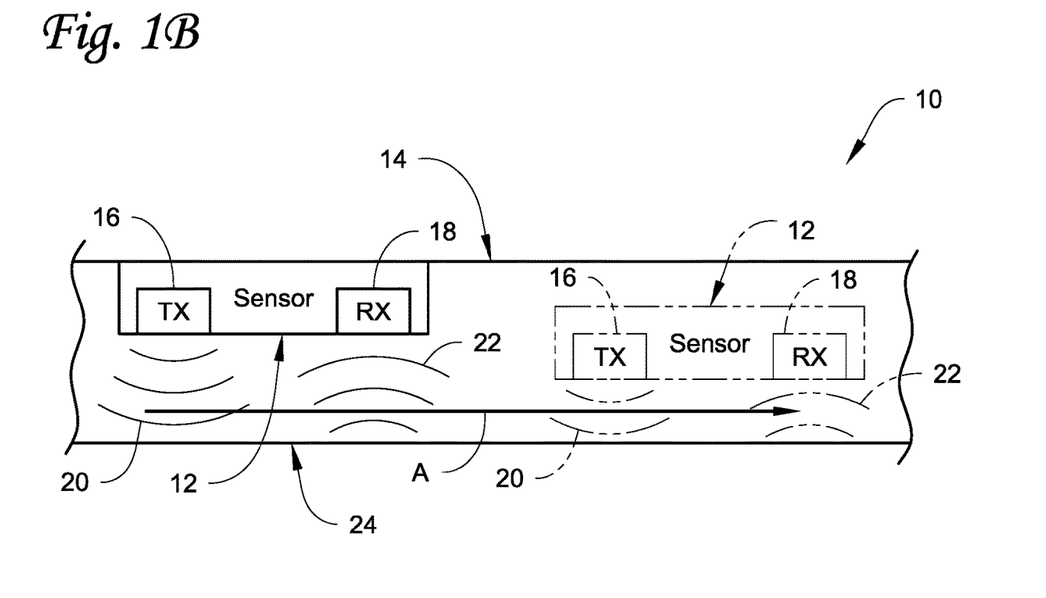
FIG. 1B is a schematic depiction similar to FIG. 1A but with the in vitro sensor positioned within the in vitro fluid passageway.

In another embodiment illustrated in FIG. 1B, the sensor 12 is positioned adjacent to the fluid passageway 14 but within the fluid passageway 14. The sensor 12 may be mounted on the interior surface of the wall of the passageway 14, or the sensor 12 may be supported in a manner so that the sensor 12 is spaced from the wall. The sensor 12 may be fully immersed in the fluid flowing through the passageway 14, the sensor 12 may be completely outside of and not wetted by the fluid flowing through the passageway 14, or the sensor 12 may be partially immersed in the fluid flowing through the passageway 14.

In general, the in vitro sensor 12 is configured to include at least one transmit antenna/element 16 and at least one receive antenna/element 18. In FIG. 1A, the antennas 16, 18 may face the fluid passageway 14. The at least one transmit antenna 16 is positioned and arranged to transmit a signal 20 into the fluid passageway 14 or into the fluid, wherein the signal is in a radio or microwave frequency range of the electromagnetic spectrum, for example between about 10 kHz to about 100 GHz. The at least one receive antenna 18 is positioned and arranged to detect a response 22 resulting from transmission of the signal 20 by the at least one transmit antenna 16 into the fluid. In some embodiments, the transmit antenna and the receive antenna are decoupled from one another which improves the detection performance of the sensor 10.

With continued reference to FIG. 1A, the fluid passageway 14 includes a sensing section 24 where the sensing of the in vitro flowing fluid by the in vitro sensor 12 takes place. At least the sensing section 24, and possibly the entire fluid passageway 14, is formed in a manner to permit travel of electromagnetic waves of the signal 20 and the response 22 that are in the radio or microwave frequency bands of the electromagnetic spectrum through at least one wall of the fluid passageway 14 and into and from the flowing fluid in the fluid passageway 14. In one embodiment, the sensing section 24 is located where the flowing fluid has laminar flow. In another embodiment, the sensing section 24 is located where the flowing fluid has turbulent flow.

The fluid passageway 14 can be a pipe, tube, conduit or the like that permits fluid to be analyzed to flow through the fluid passageway 14. The fluid passageway 14, as a whole or at the sensing section 24, can be formed from metal, plastic, glass, wood, ceramic, cardboard, paper, or other materials suitable for forming a fluid passageway 14. In one embodiment, the sensing section 24 or the portion of the sensing section 24 facing the sensor 12 is made from non-optically transparent material. In other words, the sensing section 24 that faces the sensor 12 need not be transparent to light and can be made opaque to light.

The fluid passageway 14 can be part of a closed loop fluid system where the fluid passageway 14 forms part of a recirculation path for the flowing fluid. The fluid passageway 14 may also be part of a fluid system where the flowing fluid flows from one location to another location, with the sensing section 24 and the sensor 12 located at any desired location along the fluid passageway 14. The fluid flow in fluid passageway 14 may be caused by a mechanical device, such as a pump, fan or other fluid impelling device located upstream and/or downstream of the sensing section 24. In other embodiments, the fluid flow in fluid passageway 14 may be caused by gravity.

In one embodiment, the sensor 12 can have a construction like the sensors disclosed in U.S. Pat. No. 10,548,503 which is incorporated herein by reference in its entirety. In another embodiment, the sensor 12 can have a construction like the sensors disclosed in U.S. Patent Application Publication 2019/0008422. In another embodiment, the sensor 12 can have a construction like the sensors disclosed in U.S. Patent Application Publication 2020/0187791.

The sensor 12 may also have a construction like that disclosed in U.S. Patent Application 62/951,756 filed on Dec. 20, 2019 and entitled Non-Invasive Analyte Sensor And System With Decoupled Transmit And Receive Antennas, and in U.S. Patent Application 62/971,053 filed on Feb. 6, 2020 and entitled Non-Invasive Detection Of An Analyte Using Different Combinations of Antennas That Can Transmit Or Receive, the entire contents of both applications are incorporated herein by reference.

In the sensor 12, the transmit antenna 16 transmits the signal 20, which can have at least two frequencies in the radio or microwave frequency range, toward and into the fluid passageway 14. The signal 20 with the at least two frequencies can be formed by separate signal portions, each having a discrete frequency, that are transmitted separately at separate times at each frequency. In another embodiment, the signal 20 with the at least two frequencies may be part of a complex signal that includes a plurality of frequencies including the at least two frequencies. The complex signal can be generated by blending or multiplexing multiple signals together followed by transmitting the complex signal whereby the plurality of frequencies are transmitted at the same time. One possible technique for generating the complex signal includes, but is not limited to, using an inverse Fourier transformation technique. The receive antenna 18 detects the response 22 resulting from transmission of the signal 20 by the transmit antenna 16 into the fluid passageway 14.

The transmit antenna 16 and the receive antenna 18 can be decoupled (which may also be referred to as detuned or the like) from one another. Decoupling refers to intentionally fabricating the configuration and/or arrangement of the transmit antenna 16 and the receive antenna 18 to minimize direct communication between the transmit antenna 16 and the receive antenna 18, preferably absent shielding. Shielding between the transmit antenna 16 and the receive antenna 18 can be utilized. However, the transmit antenna 16 and the receive antenna 18 are decoupled even without the presence of shielding.

Figure 2:
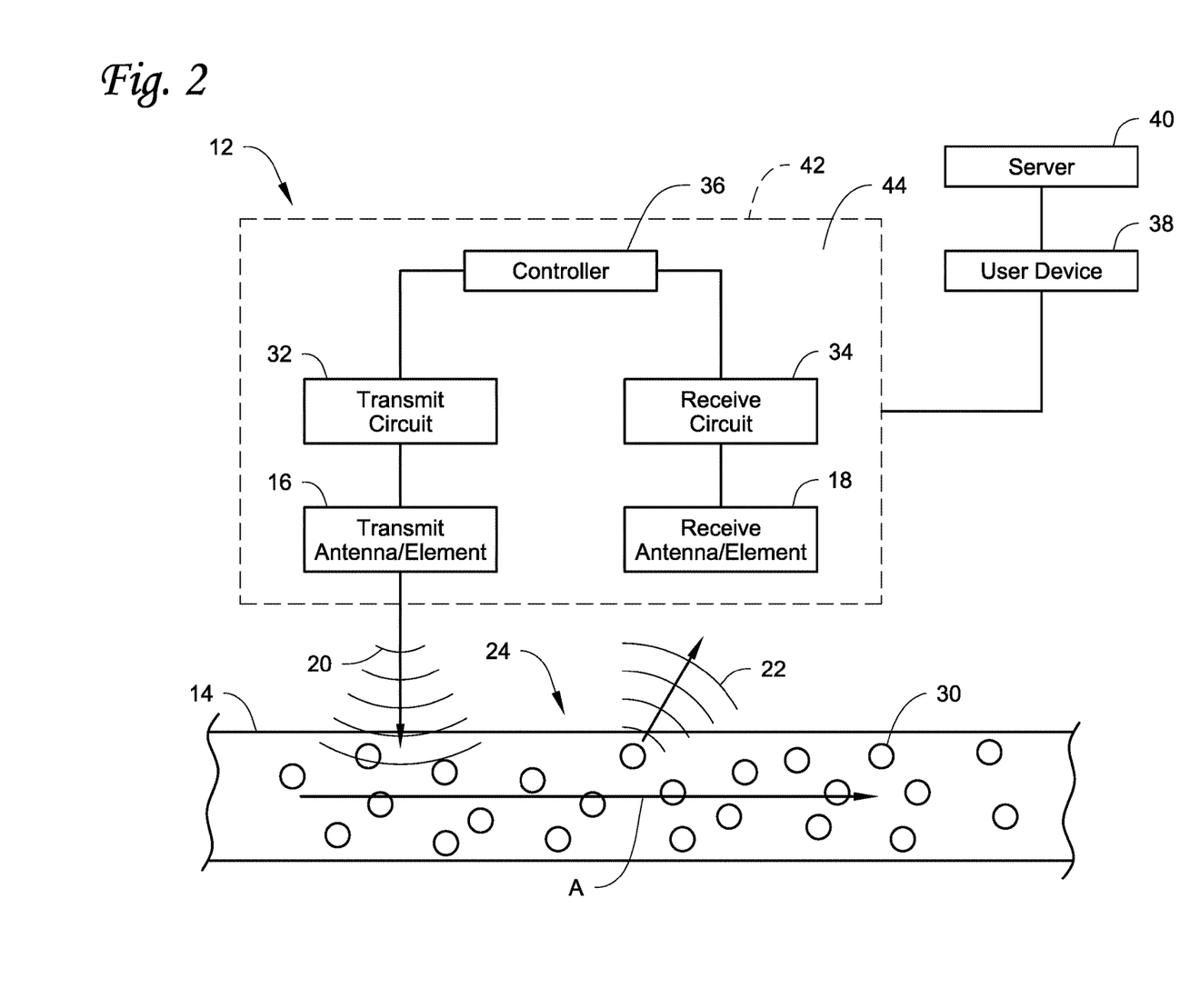
FIG. 2 is a schematic depiction of an example of the in vitro sensor that can be used.

Referring to FIG. 2, an embodiment of the sensor 12 is illustrated. In FIG. 2, elements that are the same as elements in FIG. 1 are referenced using the same reference numerals. The sensor 12 is depicted relative to the fluid passageway 14 containing the flowing fluid indicated by the arrow A. In this example, the fluid is indicated as including an analyte 30 which for sake of explanation are depicted with enlarged circles. In this example, the sensor 12 is depicted as including an antenna array that includes the transmit antenna/element 16 (hereinafter "transmit antenna 16") and the receive antenna/element 18 (hereinafter "receive antenna 18"). The sensor 12 further includes a transmit circuit 32, a receive circuit 34, and a controller 36. As discussed further below, the sensor 12 can also include a power supply, such as a battery (not shown in FIG. 2).

The transmit antenna 16 is positioned, arranged and configured to transmit the signal 20 that is the radio frequency (RF) or microwave range of the electromagnetic spectrum into the fluid passageway 14. The transmit antenna 16 can be an electrode or any other suitable transmitter of electromagnetic signals in the radio frequency (RF) or microwave range. The transmit antenna 16 can have any arrangement and orientation relative to the fluid passageway 14 that is sufficient to allow the sensing described herein to take place. In one non-limiting embodiment, the transmit antenna 16 can be arranged to face in a direction that is substantially toward the fluid passageway 14.

The signal 20 transmitted by the transmit antenna 16 is generated by the transmit circuit 32 which is electrically connectable to the transmit antenna 16. The transmit circuit 32 can have any configuration that is suitable to generate a transmit signal to be transmitted by the transmit antenna 16. Transmit circuits for generating transmit signals in the RF or microwave frequency range are well known in the art. In one embodiment, the transmit circuit 32 can include, for example, a connection to a power source, a frequency generator, and optionally filters, amplifiers or any other suitable elements for a circuit generating an RF or microwave frequency electromagnetic signal. In an embodiment, the signal generated by the transmit circuit 32 can have at least two discrete frequencies (i.e. a plurality of discrete frequencies), each of which is in the range from about 10 kHz to about 100 GHz. In another embodiment, each of the at least two discrete frequencies can be in a range from about 300 MHz to about 6000 MHz. In an embodiment, the transmit circuit 32 can be configured to sweep through a range of frequencies that are within the range of about 10 kHz to about 100 GHz, or in another embodiment a range of about 300 MHz to about 6000 MHz. In an embodiment, the transmit circuit 32 can be configured to produce a complex transmit signal, the complex signal including a plurality of signal components, each of the signal components having a different frequency. The complex signal can be generated by blending or multiplexing multiple signals together followed by transmitting the complex signal whereby the plurality of frequencies are transmitted at the same time.

The receive antenna 18 is positioned, arranged, and configured to detect the one or more electromagnetic response signals 22 that result from the transmission of the transmit signal 20 by the transmit antenna 16 into the fluid passageway 14. The receive antenna 18 can be an electrode or any other suitable receiver of electromagnetic signals in the radio frequency (RF) or microwave range. In an embodiment, the receive antenna 18 is configured to detect electromagnetic signals having at least two frequencies, each of which is in the range from about 10 kHz to about 100 GHz, or in another embodiment a range from about 300 MHz to about 6000 MHz. The receive antenna 18 can have any arrangement and orientation relative to the fluid passageway 14 that is sufficient to allow detection of the response signal(s) 22 to allow the sensing described herein to take place. In one non-limiting embodiment, the receive antenna 18 can be arranged to face in a direction that is substantially toward the fluid passageway 14.

The receive circuit 34 is electrically connectable to the receive antenna 18 and conveys the received response from the receive antenna 18 to the controller 36. The receive circuit 34 can have any configuration that is suitable for interfacing with the receive antenna 18 to convert the electromagnetic energy detected by the receive antenna 18 into one or more signals reflective of the response signal(s) 22. The construction of receive circuits are well known in the art. The receive circuit 34 can be configured to condition the signal(s) prior to providing the signal(s) to the controller 36, for example through amplifying the signal(s), filtering the signal(s), or the like. Accordingly, the receive circuit 34 may include filters, amplifiers, or any other suitable components for conditioning the signal(s) provided to the controller 36. In an embodiment, at least one of the receive circuit 34 or the controller 36 can be configured to decompose or demultiplex a complex signal, detected by the receive antenna 18, including a plurality of signal components each at different frequencies into each of the constituent signal components. In an embodiment, decomposing the complex signal can include applying a Fourier transform to the detected complex signal. However, decomposing or demultiplexing a received complex signal is optional. Instead, in an embodiment, the complex signal detected by the receive antenna can be analyzed as a whole (i.e. without demultiplexing the complex signal) to detect the analyte as long as the detected signal provides enough information to make the analyte detection.

The controller 36 controls the operation of the sensor 12. The controller 36, for example, can direct the transmit circuit 32 to generate a transmit signal to be transmitted by the transmit antenna 16. The controller 36 further receives signals from the receive circuit 34. The controller 36 can optionally process the signals from the receive circuit 34 to perform the detection described herein. In one embodiment, the controller 36 may optionally be in communication with at least one external device 38 such as a user device and/or a remote server 40, for example through one or more wireless connections such as Bluetooth, wireless data connections such a 4G, 5G, LTE or the like, or Wi-Fi. If provided, the external device 38 and/or remote server 40 may process (or further process) the signals that the controller 36 receives from the receive circuit 34. If provided, the external device 38 may be used to provide communication between the sensor 12 and the remote server 40, for example using a wired data connection or via a wireless data connection or Wi-Fi of the external device 38 to provide the connection to the remote server 40.

With continued reference to FIG. 2, the sensor 12 may include a sensor housing 42 (shown in dashed lines) that defines an interior space 44. Components of the sensor 12 may be attached to and/or disposed within the housing 42. For example, the transmit antenna 16 and the receive antenna 18 are attached to the housing 42. In some embodiments, the antennas 16, 18 may be entirely or partially within the interior space 44 of the housing 42. In some embodiments, the antennas 16, 18 may be attached to the housing 42 but at least partially or fully located outside the interior space 44. In some embodiments, the transmit circuit 32, the receive circuit 34 and the controller 36 are attached to the housing 42 and disposed entirely within the sensor housing 42.

The receive antenna 18 may be decoupled or detuned with respect to the transmit antenna 16 such that electromagnetic coupling between the transmit antenna 16 and the receive antenna 18 is reduced. The decoupling of the transmit antenna 16 and the receive antenna 18 increases the portion of the signal(s) detected by the receive antenna 16 that is the response signal(s) 22 from the fluid passageway 14, and minimizes direct receipt of the transmitted signal 20 by the receive antenna 18. The decoupling of the transmit antenna 16 and the receive antenna 18 results in transmission from the transmit antenna 16 to the receive antenna 18 having a reduced forward gain (S21) and an increased reflection at output (S22) compared to antenna systems having coupled transmit and receive antennas.

In an embodiment, coupling between the transmit antenna 16 and the receive antenna 18 is 95% or less. In another embodiment, coupling between the transmit antenna 16 and the receive antenna 18 is 90% or less. In another embodiment, coupling between the transmit antenna 16 and the receive antenna 18 is 85% or less. In another embodiment, coupling between the transmit antenna 16 and the receive antenna 18 is 75% or less.

Any technique for reducing coupling between the transmit antenna 16 and the receive antenna 18 can be used. For example, the decoupling between the transmit antenna 16 and the receive antenna 18 can be achieved by one or more intentionally fabricated configurations and/or arrangements between the transmit antenna 16 and the receive antenna 18 that is sufficient to decouple the transmit antenna 16 and the receive antenna 18 from one another.

For example, in one embodiment, the decoupling of the transmit antenna 16 and the receive antenna 18 can be achieved by intentionally configuring the transmit antenna 16 and the receive antenna 18 to have different geometries from one another. Intentionally different geometries refers to different geometric configurations of the transmit and receive antennas 16, 18 that are intentional. Intentional differences in geometry are distinct from differences in geometry of transmit and receive antennas that may occur by accident or unintentionally, for example due to manufacturing errors or tolerances.

Another technique to achieve decoupling of the transmit antenna 16 and the receive antenna 18 is to provide appropriate spacing between each antenna 16, 18 that is sufficient to decouple the antennas 16, 18 and force a proportion of the electromagnetic lines of force of the transmitted signal 20 into the fluid passageway 14 thereby minimizing or eliminating as much as possible direct receipt of electromagnetic energy by the receive antenna 18 directly from the transmit antenna 16 without traveling into the fluid passageway. The appropriate spacing between each antenna 16, 18 can be determined based upon factors that include, but are not limited to, the output power of the signal from the transmit antenna 16, the size of the antennas 16, 18, the frequency or frequencies of the transmitted signal, and the presence of any shielding between the antennas. This technique helps to ensure that the response detected by the receive antenna 18 is performing the desired sensing and is not just the transmitted signal 20 flowing directly from the transmit antenna 16 to the receive antenna 18. In some embodiments, the appropriate spacing between the antennas 16, 18 can be used together with the intentional difference in geometries of the antennas 16, 18 to achieve decoupling.

In one embodiment, the transmit signal that is transmitted by the transmit antenna 16 can have at least two different frequencies, for example upwards of 7 to 12 different and discrete frequencies. In another embodiment, the transmit signal can be a series of discrete, separate signals with each separate signal having a single frequency or multiple different frequencies.

In one embodiment, the transmit signal (or each of the transmit signals) can be transmitted over a transmit time that is less than, equal to, or greater than about 300 ms. In another embodiment, the transmit time can be than, equal to, or greater than about 200 ms. In still another embodiment, the transmit time can be less than, equal to, or greater than about 30 ms. The transmit time could also have a magnitude that is measured in seconds, for example 1 second, 5 seconds, 10 seconds, or more. In an embodiment, the same transmit signal can be transmitted multiple times, and then the transmit time can be averaged. In another embodiment, the transmit signal (or each of the transmit signals) can be transmitted with a duty cycle that is less than or equal to about 50%.

Figure 3:
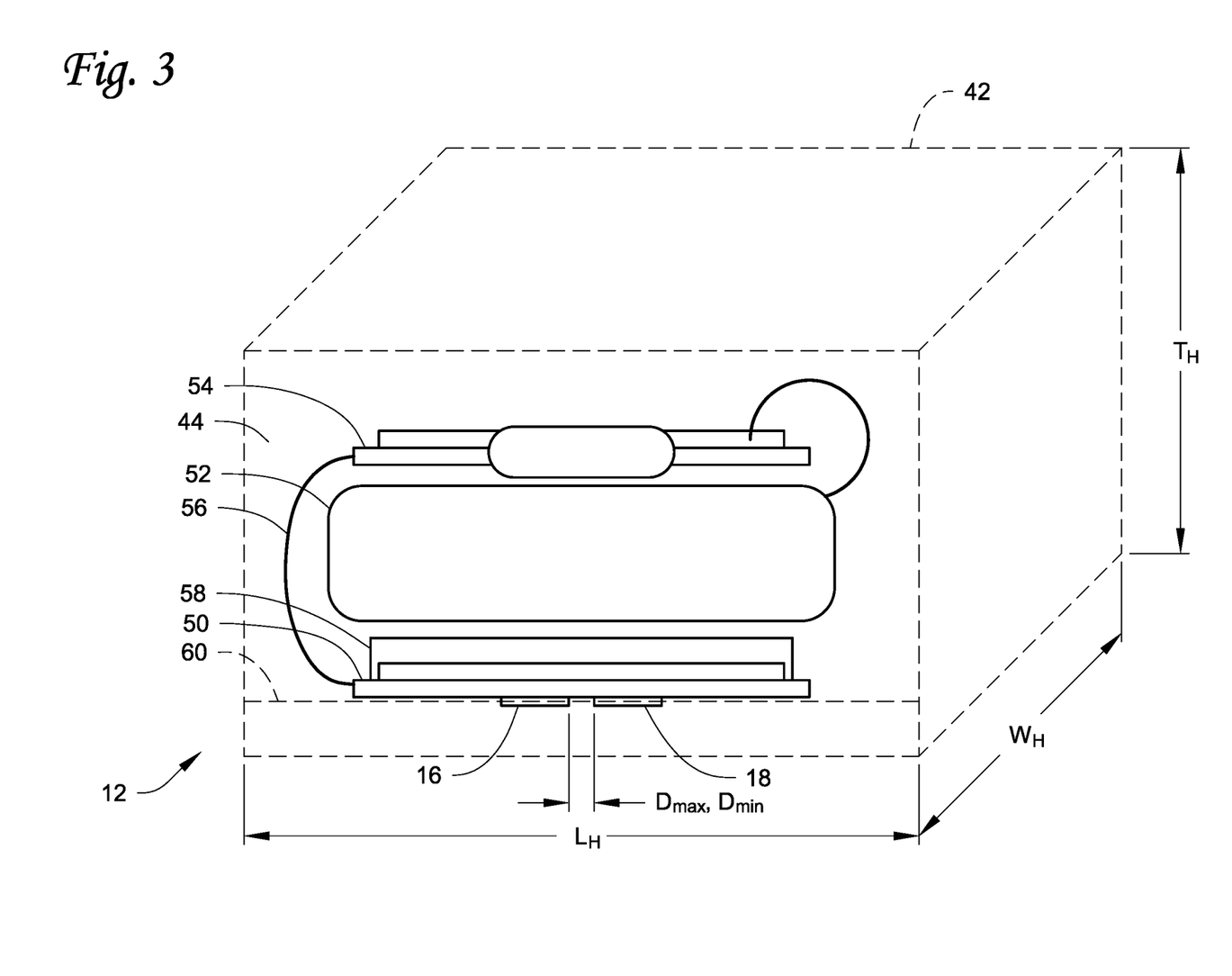
FIG. 3 is a schematic depiction of the in vitro sensor according to an embodiment.
Figure 4:
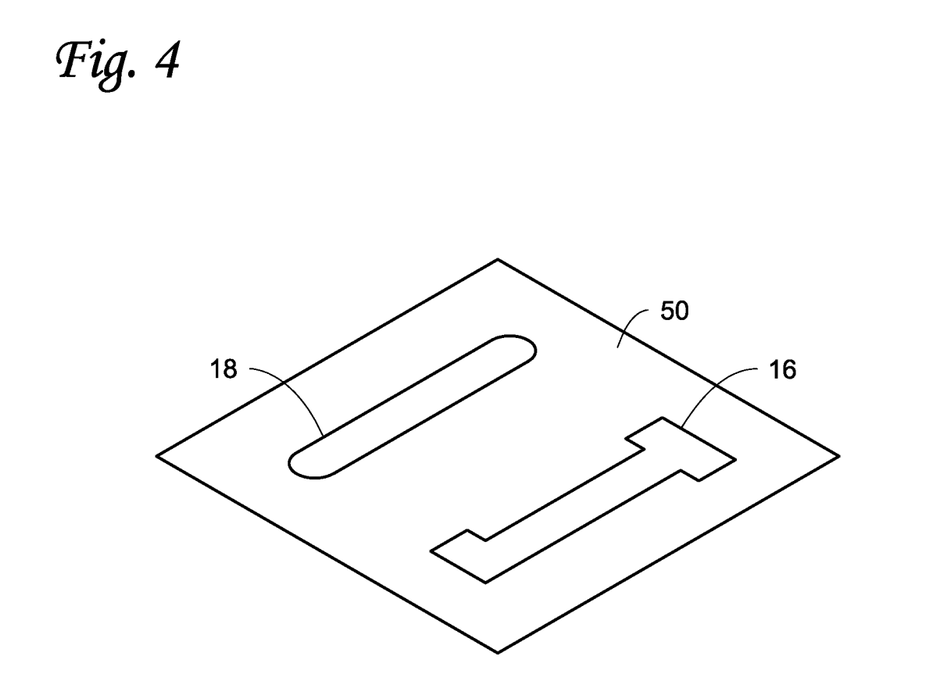
FIG. 4 depicts an example of an antenna array that can be used in the in vitro sensor.

Referring to FIG. 3, an example configuration of the sensor 12 is illustrated. In FIG. 3, elements that are identical or similar to elements in FIGS. 1 and 2 are referenced using the same reference numerals. In FIG. 3, the antennas 16, 18 are disposed on one surface of a substrate 50 which can be, for example, a printed circuit board. FIG. 4 illustrates an example of the antennas 16, 18 in the form of metal traces disposed on the substrate 50. Returning to FIG. 3, at least one battery 52, such as a rechargeable battery, is provided above the substrate 50, for providing power to the sensor 12. In addition, a digital printed circuit board 54 is provided on which the transmit circuit, the receive circuit, and the controller and other electronics of the sensor 12 can be disposed. The substrate 50 and the digital printed circuit board 54 are electrically connected via any suitable electrical connection, such as a flexible connector 56. An RF shield 58 may optionally be positioned between the antennas 16, 18 and the battery 52, or between the antennas 16, 18 and the digital printed circuit board 54, to shield the circuitry and electrical components from RF interference.

As depicted in FIG. 3, all of the elements of the sensor 12, including the antennas 16, 18, the transmit circuit, the receive circuit, the controller, the battery 52 and the like are contained entirely within the interior space 44 of the housing 42. In an alternative embodiment, a portion of or the entirety of each antenna 16, 18 can project below a bottom wall 60 of the housing 42. In another embodiment, the bottom of each antenna 16, 18 can be level with the bottom wall 60, or they can be slightly recessed from the bottom wall 60.

The housing 42 of the sensor 10 can have any configuration and size that one finds suitable for employing in the sensor 10 described herein. In one embodiment, the housing 42 can have a maximum length dimension $L_H$ no greater than 50 mm, a maximum width dimension $W_H$ no greater than 50 mm, and a maximum thickness dimension TH no greater than 25 mm, for a total interior volume of no greater than about 62.5 cm$^3$. However, other dimensions are possible.

In addition, with continued reference to FIG. 3, there can be a maximum spacing $D_{max}$ and a minimum spacing $D_{min}$ between the transmit antenna 16 and the receive antenna 18. The maximum spacing $D_{max}$ may be dictated by the maximum size of the housing 42. In one embodiment, the maximum spacing $D_{max}$ can be about 50 mm. In one embodiment, the minimum spacing $D_{min}$ can be from about 1.0 mm to about 5.0 mm.

The analysis of the in vitro flowing fluid, by the sensor 12 or by an external device using data obtained by the sensor 12, can include, but is not limited to, one or more of the following: determining the presence and/or amount of an analyte, such as the analyte 30 in FIG. 3, in the in vitro flowing fluid; determining a steady state condition of the in vitro flowing fluid as reflected in a steady state condition of the detected response(s); determining a change in condition of the in vitro flowing fluid as reflected in a change of the detected response(s). Other analyses are possible.

For example, in some embodiments, the response or signal(s) 22 detected by the receive antenna 18 can be analyzed to detect the analyte 30 in the flowing fluid based on the intensity of the received signal(s) and reductions in intensity at one or more frequencies where the analyte absorbs the transmitted signal. The signal(s) detected by the receive antenna can be complex signals including a plurality of signal components, each signal component being at a different frequency. In an embodiment, the detected complex signals can be decomposed into the signal components at each of the different frequencies, for example through a Fourier transformation. In an embodiment, the complex signal detected by the receive antenna can be analyzed as a whole (i.e. without demultiplexing the complex signal) to detect the analyte as long as the detected signal provides enough information to make the analyte detection. In addition, the signal(s) detected by the receive antenna can be separate signal portions, each having a discrete frequency.

In one embodiment, the sensor 12 can be used to detect the presence of at least one analyte in the flowing fluid. In another embodiment, the sensor can detect an amount or a concentration of the at least one analyte in the flowing fluid. The analyte(s) can be any analyte that one may wish to detect. The analyte can be human or non-human, animal or non-animal, biological or non-biological. For example, the analyte(s) can include, but is not limited to, one or more of blood glucose, blood cholesterol, blood alcohol, white blood cells, or luteinizing hormone. The analyte(s) can include, but is not limited to, a chemical, a combination of chemicals, a virus, bacteria, or the like. The analyte can be a chemical included in another medium, with non-limiting examples of such media including a fluid containing the at least one analyte, for example blood, interstitial fluid, cerebral spinal fluid, lymph fluid or urine. The analyte(s) may also be a non-human, non-biological particle such as a mineral or a contaminant.

The analyte(s) that can be detected can include, for example, naturally occurring substances, artificial substances, metabolites, and/or reaction products. As non-limiting examples, the at least one analyte can include, but is not limited to, insulin, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (for example, DNA associated with acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, or 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (such as antibodies for or associated with an adenovirus, anti-nuclear antibodies, anti-zeta antibodies, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, polio virus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

The analyte(s) can also include one or more chemicals introduced into the flowing fluid. The analyte(s) can include a marker such as a contrast agent, a radioisotope, or other chemical agent. The analyte(s) can include a fluorocarbon-based synthetic blood. The analyte(s) can include a drug or pharmaceutical composition, with non-limiting examples including ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The analyte(s) can include other drugs or pharmaceutical compositions. The analyte(s) can include neurochemicals or other chemicals generated within the body, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

Figure 5:
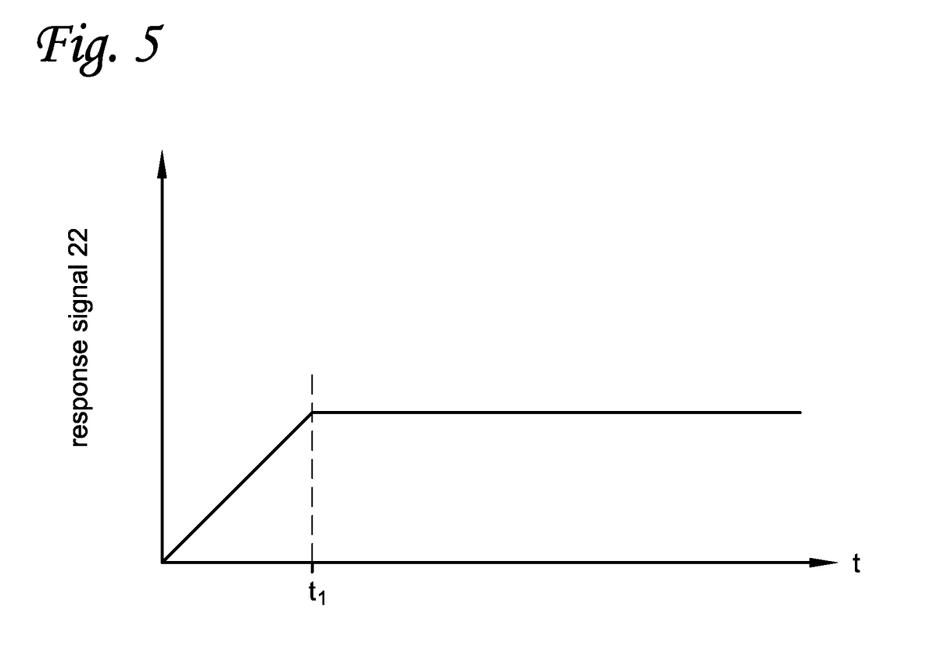
FIG. 5 illustrates an example of a response detected by the receive antenna.

FIG. 5 depicts an example of an analysis that involves determining a steady state condition of the in vitro flowing fluid as reflected in a steady state condition of the detected response(s). FIG. 5 depicts an example of the response signal 22 plotted versus time. In this example, the response signal 22 is shown as changing up to time $t_1$ and then remaining substantially steady after time $t_1$. The analysis using the sensor 12 can include looking for the response signal 22 to reach a steady state which can indicate a desired condition of the flowing fluid in the fluid passageway. A desired condition can include, but is not limited to, an analyte reaching a steady state level in a fluid that carries the analyte.

Figure 6:
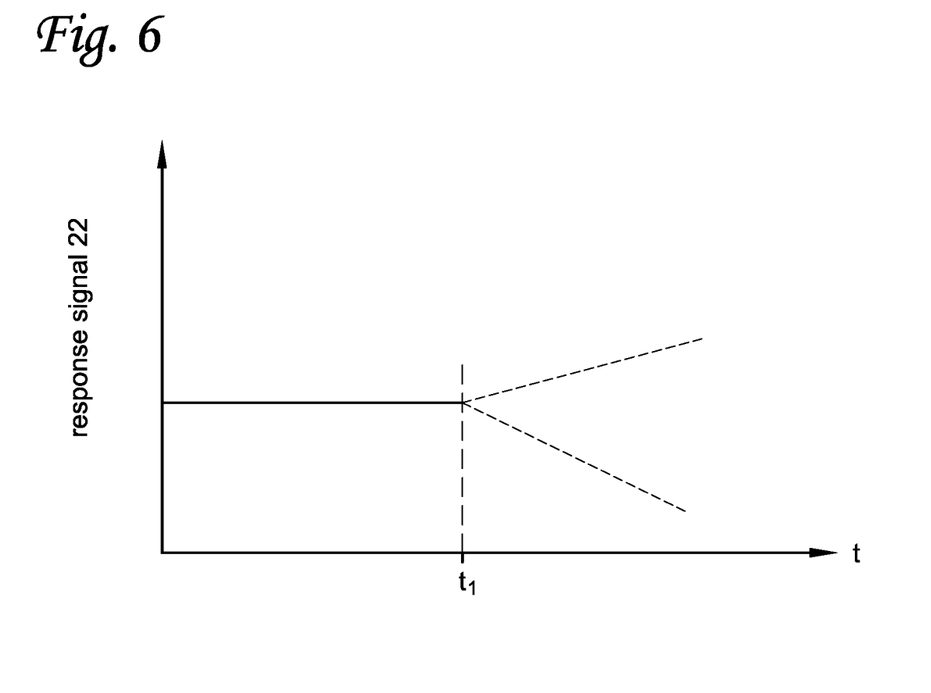
FIG. 6 illustrates another example of a response detected by the receive antenna.

FIG. 6 depicts an example of an analysis that involves determining a change in condition of the in vitro flowing fluid as reflected in a change of the detected response signal 22. FIG. 6 depicts an example of the response signal 22 plotted versus time. In this example, the response signal 22 is shown as remaining steady up to time $t_1$ at which time the signal changes significantly in some manner (FIG. 6 depicts the signal 22 increasing or decreasing at time $t_1$). The analysis using the sensor 12 can include looking for a change in the response signal 22 which can indicate a significant and perhaps undesired change in the flowing fluid in the fluid passageway. A change in the flowing fluid can include, but is not limited to, a significant change occurring in the presence or amount of an analyte in a fluid that carries the analyte.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. An in vitro sensing system, comprising:
   an in vitro sensor that is positioned adjacent to an in vitro fluid passageway that contains an in vitro flowing fluid; and
   the in vitro sensor includes:
      at least one transmit antenna and at least one receive antenna, the at least one transmit antenna is positioned and arranged to transmit a signal into the in vitro flowing fluid in the in vitro fluid passageway, wherein the signal is in a radio or microwave frequency range of the electromagnetic spectrum, and the at least one receive antenna is positioned and arranged to detect a response resulting from transmission of the signal by the at least one transmit antenna into the in vitro flowing fluid,
      wherein the at least one transmit antenna consists of a strip of conductive material having at least one lateral dimension thereof greater than a thickness dimension thereof, the strip of conductive material of the at least one transmit antenna is disposed on a substrate,
      the at least one receive antenna consists of a strip of conductive material having at least one lateral dimension thereof greater than a thickness dimension thereof, the strip of conductive material of the at least one receive antenna is disposed on the substrate,
      the at least one transmit antenna and the at least one receive antenna are coplanar with one another, and
      a geometry of the at least one transmit antenna differs from a geometry of the at least one receive antenna.

2. The in vitro sensing system of claim 1, wherein the in vitro sensor further includes:
   a transmit circuit that is electrically connectable to the at least one transmit antenna, the transmit circuit is configured to generate the signal to be transmitted by the at least one transmit antenna; and a receive circuit that is electrically connectable to the at least one receive antenna, the receive circuit is configured to receive a response detected by the at least one receive antenna.

3. The in vitro sensing system of claim 1, wherein the radio or microwave frequency range is between about 10 kHz to about 100 GHz.

4. The in vitro sensing system of claim 1, wherein the in vitro flowing fluid comprises a liquid as a primary component.

5. The in vitro sensing system of claim 1, wherein the in vitro flowing fluid comprises a gas as a primary component.

6. The in vitro sensing system of claim 1, wherein the in vitro flowing fluid comprises a nonbodily fluid as a primary component.

7. The in vitro sensing system of claim 1, wherein the in vitro flowing fluid where the signal is transmitted into has laminar flow.

8. The in vitro sensing system of claim 1, wherein the in vitro sensor is located outside the in vitro fluid passageway, the at least one transmit antenna and the at least one receive antenna face the in vitro fluid passageway, and at least a portion of the in vitro fluid passageway facing the at least one transmit antenna and the at least one receive antenna is formed from a non-optically transparent material.

9. The in vitro sensing system of claim 1, wherein the in vitro sensor is located inside the in vitro fluid passageway and the in vitro sensor is at least partially immersed in the in vitro flowing fluid.

10. An in vitro sensing system configured to sense an analyte in an in vitro flowing fluid, comprising:
   an in vitro sensor that is positioned adjacent to an in vitro fluid passageway that contains the in vitro flowing fluid with the analyte; and
   the in vitro sensor includes:
      at least one transmit element and at least one receive element, the at least one transmit element is positioned and arranged to transmit a signal into the in vitro flowing fluid in the in vitro fluid passageway, wherein the signal is in a radio or microwave frequency range of the electromagnetic spectrum that is between about 10 kHz to about 100 GHz, and the at least one receive element is positioned and arranged to detect a response resulting from transmission of the signal by the at least one transmit element into the in vitro flowing fluid,
      wherein the at least one transmit element consists of a strip of conductive material having at least one lateral dimension thereof greater than a thickness dimension thereof, the strip of conductive material of the at least one transmit element is disposed on a substrate,
      the at least one receive element consists of a strip of conductive material having at least one lateral dimension thereof greater than a thickness dimension thereof, the strip of conductive material of the at least one receive element is disposed on the substrate,
      the at least one transmit element and the at least one receive element are coplanar with one another, and
      a geometry of the at least one transmit element differs from a geometry of the at least one receive element.

11. The in vitro sensing system of claim 10, wherein the in vitro sensor further includes a transmit circuit that is electrically connectable to the at least one transmit element, the transmit circuit is configured to generate the signal to be transmitted by the at least one transmit element; and
   a receive circuit that is electrically connectable to the at least one receive element, the receive circuit is configured to receive a response detected by the at least one receive element.

12. The in vitro sensing system of claim 10, wherein the in vitro flowing fluid comprises a liquid as a primary component.

13. The in vitro sensing system of claim 10, wherein the in vitro flowing fluid comprises a gas as a primary component.

14. The in vitro sensing system of claim 10, wherein the in vitro flowing fluid comprises a non-bodily fluid as a primary component.

15. The in vitro sensing system of claim 10, wherein the in vitro flowing fluid where the signal is transmitted into has laminar flow.

16. The in vitro sensing system of claim 10, wherein the in vitro sensor is located outside the in vitro fluid passageway, the at least one transmit antenna and the at least one receive antenna face the in vitro fluid passageway, and at least a portion of the in vitro fluid passageway facing the at least one transmit antenna and the at least one receive antenna is formed from a non-optically transparent material.

17. The in vitro sensing system of claim 10, wherein the in vitro sensor is located inside the in vitro fluid passageway such that the in vitro sensor is at least partially immersed in the in vitro flowing fluid.

18. The in vitro sensing system of claim 10, wherein the analyte in the in vitro flowing fluid comprises cholesterol, blood glucose, blood alcohol, white blood cells, or luteinizing hormone.

19. The in vitro sensing system of claim 2, wherein the in vitro sensor further comprises a battery and the at least one transmit antenna, the transmit circuit, the at least one receive antenna, the receive circuit, and the battery are all disposed in a housing.

20. The in vitro sensing system of claim 11, wherein the in vitro sensor further comprises a battery and the at least one transmit element, the transmit circuit, the at least one receive element, the receive circuit, and the battery are all disposed in a housing.

* * * * *